United States Patent
Okuda et al.

(10) Patent No.: US 10,434,016 B2
(45) Date of Patent: Oct. 8, 2019

(54) MANUFACTURING APPARATUS AND MANUFACTURING METHOD OF SHEET-LIKE MEMBER OF ABSORBENT ARTICLE

(71) Applicant: UNICHARM Corporation, Ehime (JP)

(72) Inventors: Jun Okuda, Kagawa (JP); Satoshi Mitsuno, Kagawa (JP)

(73) Assignee: UNICHARM CORPORATION, Ehime (JP)

( * ) Notice: Subject to any disclaimer, the term of this patent is extended or adjusted under 35 U.S.C. 154(b) by 586 days.

(21) Appl. No.: 15/029,245

(22) PCT Filed: Sep. 22, 2014

(86) PCT No.: PCT/JP2014/075102
§ 371 (c)(1),
(2) Date: Apr. 13, 2016

(87) PCT Pub. No.: WO2015/056533
PCT Pub. Date: Apr. 23, 2015

(65) Prior Publication Data
US 2016/0235591 A1   Aug. 18, 2016

(30) Foreign Application Priority Data
Oct. 18, 2013   (JP) .................. 2013-217204

(51) Int. Cl.
*B64D 5/00* (2006.01)
*G05D 1/10* (2006.01)
(Continued)

(52) U.S. Cl.
CPC ...... *A61F 13/15699* (2013.01); *A01K 1/0157* (2013.01); *B32B 38/00* (2013.01);
(Continued)

(58) Field of Classification Search
CPC .............. A61F 13/15699; B32B 38/00; B32B 2398/20; B32B 2305/20; B32B 2038/0088; A01K 1/0157
(Continued)

(56) References Cited

U.S. PATENT DOCUMENTS

| | | | | |
|---|---|---|---|---|
| 6,502,625 B2 * | 1/2003 | Pullum | .................. | B22D 15/04 164/264 |
| 7,028,735 B2 * | 4/2006 | Schneider | ............. | B32B 37/144 156/436 |

(Continued)

FOREIGN PATENT DOCUMENTS

| CN | 1497086 A | 5/2004 |
|---|---|---|
| CN | 1824867 A | 8/2006 |

(Continued)

OTHER PUBLICATIONS

International Search Report in PCT/JP2014/075102, dated Nov. 25, 2014.

(Continued)

*Primary Examiner* — Michael N Orlando
*Assistant Examiner* — Christian Roldan
(74) *Attorney, Agent, or Firm* — Hauptman Ham, LLP

(57) ABSTRACT

A manufacturing apparatus is provided to manufacture a sheet-like member by joining a non-woven fabric to another member of an absorbent article. This apparatus includes a bulk restoring device that restores bulk of the non-woven fabric through heating the non-woven fabric by blowing hot wind onto the non-woven fabric while conveying the non-woven fabric along a conveying direction, the non-woven fabric being continuous in the conveying direction, and a joining device that joins the non-woven fabric whose bulk has been restored with the hot wind to the other member using an adhesive, the non-woven fabric being at a higher (Continued)

temperature than a temperature before being heated with the hot wind.

10 Claims, 6 Drawing Sheets

(51) Int. Cl.
  *B64C 39/02* (2006.01)
  *A61F 13/15* (2006.01)
  *A01K 1/015* (2006.01)
  *B32B 38/00* (2006.01)

(52) U.S. Cl.
  CPC ... *B32B 2038/0088* (2013.01); *B32B 2305/20* (2013.01); *B32B 2398/20* (2013.01)

(58) Field of Classification Search
  USPC .......................................................... 156/285
  See application file for complete search history.

(56) References Cited

U.S. PATENT DOCUMENTS

| | | | |
|---|---|---|---|
| 7,131,171 B2 * | 11/2006 | Miyamoto | A61F 13/15699 28/166 |
| 2002/0193765 A1 * | 12/2002 | Kudo | A61F 13/15699 604/378 |

FOREIGN PATENT DOCUMENTS

| | | |
|---|---|---|
| CN | 101553611 A | 10/2009 |
| CN | 102373595 A | 3/2012 |
| EP | 1269956 A2 | 1/2003 |
| EP | 1403413 A1 | 3/2004 |
| EP | 2602372 A1 | 6/2013 |
| JP | 5-35856 U | 5/1993 |
| JP | 6-158499 A | 6/1994 |
| JP | 2003-339761 A | 12/2003 |
| JP | 2004-137655 A | 5/2004 |
| JP | 2008-156793 A | 7/2008 |
| JP | 2010-156076 A | 7/2010 |
| JP | 2012-249953 A | 12/2012 |

OTHER PUBLICATIONS

Office Action in EP Application No. 14854390.3, dated Apr. 5, 2017.
Office Action in JP Application No. 2015-94039, dated Apr. 25, 2017.
Extended European Search Report in EP Application No. 14854390.3, dated Sep. 9, 2016.
Written Opinion in International Patent Application No. PCT/JP20141075102, dated Nov. 25, 2014.

* cited by examiner

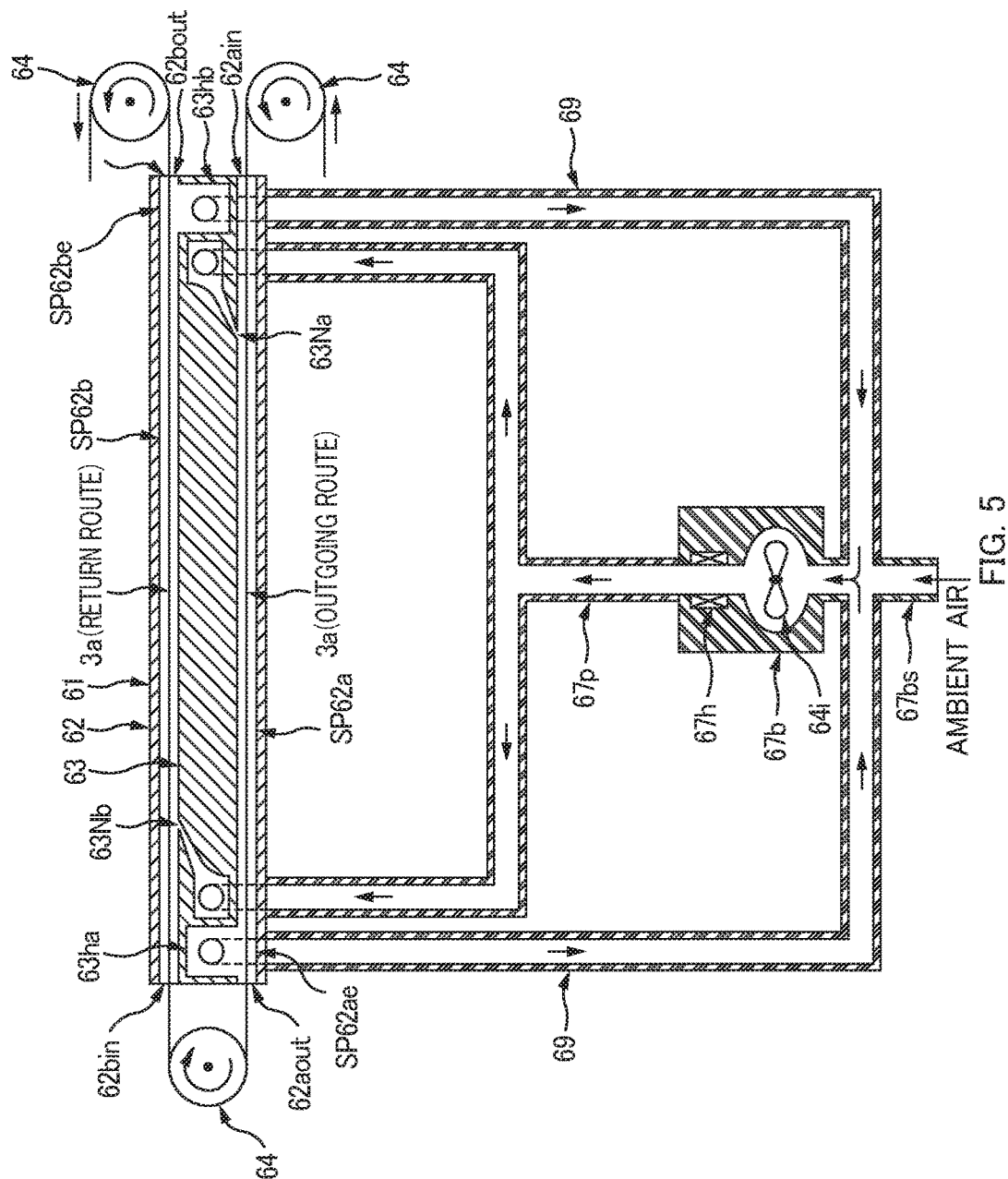

MANUFACTURING APPARATUS AND MANUFACTURING METHOD OF SHEET-LIKE MEMBER OF ABSORBENT ARTICLE

RELATED APPLICATIONS

The present application is a National Phase entry of International Application No. PCT/JP2014/075102, filed Sep. 22, 2014, which claims priority of Japanese Application No. 2013-217204, filed Oct. 18, 2013.

Technical Field

The present invention relates to a manufacturing apparatus and a manufacturing method of a sheet-like member of an absorbent article such as a pet sheet.

Background Art

Conventionally, sanitary napkins and disposable diapers have been used as absorbent articles. Pet sheets, which are included in the same category, are also widely used as a toilet for pets.

A liquid-permeable top sheet is provided in the portions of such absorbent articles that come into contact with the user's skin or the like. Furthermore, high liquid draining performance has recently been demanded for top sheets from the viewpoint of reducing the sense of stickiness to skin for example, and bulky non-woven fabric is considered to be favorable as such a material.

Such non-woven fabric is manufactured in a long strip using an appropriate method such as carding, and then wound into a roll and stored in the form of a non-woven fabric whole cloth. When the time to be used arrives, the non-woven fabric whole cloth is carried to the absorbent article manufacturing line, and the non-woven fabric is fed from the whole cloth in the line and used as the top sheet material.

When non-woven fabric is wound into a non-woven fabric whole cloth, tension is applied in the winding direction during winding in order to prevent the non-woven fabric from zigzagging or the like. For this reason, non-woven fabric is normally wound tightly due to this tension. Specifically, the non-woven fabric is compressed in the thickness direction and has reduced bulk. Accordingly, when the non-woven fabric is fed from the non-woven fabric whole cloth in the absorbent article manufacturing line, non-woven fabric having reduced bulk is merely fed and supplied, and in other words it is not possible to meet the aforementioned demand for bulky non-woven fabric.

To address this problem, Patent Document 1 discloses a technique in which a bulk restoring device is installed upstream in the absorbent article manufacturing line. Specifically, there is disclosed that non-woven fabric fed from a non-woven fabric whole cloth is heated by hot wind being blown thereon with a bulk restoring device when the non-woven fabric passes through a predetermined conveying route, and thus the bulk of the non-woven fabric is restored. There is also disclosed that the non-woven fabric is cooled with cool wind immediately after the aforementioned heating, and then the non-woven fabric with restored bulk is sent as-is, without being wound again, to the next processing apparatus in the manufacturing line.

CITATION LIST

Patent Document

[Patent Document 1] Japanese Patent Application Laid-open Publication No. 2004-137655

SUMMARY

Technical Problem

In the case where the non-woven fabric is joined to another member using an adhesive instead of welding in the next processing apparatus, however, the aforementioned cooling reduces the temperature of the non-woven fabric, thus increasing the viscosity of the adhesive and reducing its fluidity, and the adhesive no longer smoothly impregnates and permeates the non-woven fabric. For example, in the case where the other member is a fibrous member having many fibers such as tissue paper, if the impregnation and permeation of the adhesive does not proceed smoothly, the area occupied with the adhesive (referred to hereinafter as the "adhered area") on both the surface of the fibers in the non-woven fabric and the surface of the fibers in the other member will decrease as shown in FIG. 6A. As a result, the strength of adhesion between the non-woven fabric and the other member decreases.

Thus, in this case, it is necessary to perform separate processing for compensating for the reduction in adhesion strength. As one example of this, the combined material including the non-woven fabric and the other member is inserted between a pair of upper and lower press rolls and pressed in the thickness direction. Specifically, the adhesive is forcibly caused to spread by the pressing, and the adhered area (i.e., the area where the adhesive is present) can be considered to expand on both the surface of the fibers in the non-woven fabric and the surface of the fibers in the other member as shown in FIG. 6B. When pressing is performed excessively, however, the bulk of the non-woven fabric is lost.

The present invention was achieved in light of conventional problems such as those described above, and an objective is to make it possible to join a non-woven fabric having restored bulk to another member with high adhesion strength, while also substantially keeping the non-woven fabric in a bulky state.

Solution to Problem

A main invention for achieving the aforementioned object is a manufacturing apparatus of a sheet-like member of an absorbent article to manufacture the sheet-like member by joining a non-woven fabric to another member of the absorbent article, the manufacturing apparatus including:

a bulk restoring device that restores bulk of the non-woven fabric through heating the non-woven fabric by blowing hot wind onto the non-woven fabric while conveying the non-woven fabric along a conveying direction, the non-woven fabric being continuous in the conveying direction; and a joining device that joins the non-woven fabric whose bulk has been restored with the hot wind to the other member using an adhesive, the non-woven fabric being at a higher temperature than a temperature before being heated with the hot wind.

Also, a manufacturing method of a sheet-like member of an absorbent article to manufacture the sheet-like member by joining a non-woven fabric to another member of the absorbent article, the manufacturing method including:

restoring bulk of the non-woven fabric through heating the non-woven fabric by blowing hot wind onto the non-woven fabric while conveying the non-woven fabric along a conveying direction, the non-woven fabric being continuous in the conveying direction; and joining the non-woven fabric whose bulk has been restored with the hot wind to the other member using an adhesive, the non-woven fabric being at a higher temperature than a temperature before being heated with the hot wind.

Other features of the present invention will become evident from the description of this specification and the accompanying drawings.

Advantageous Effects of Invention

According to the present invention, it is possible to join a non-woven fabric having restored bulk to another member with high adhesion strength, while also substantially keeping the non-woven fabric in a bulky state.

BRIEF DESCRIPTION OF THE DRAWINGS

FIG. 5 is a schematic cross-sectional view of a configuration for recovering hot wind flowing through outgoing route and return route spaces SP62a and SP62b and returning it to an intake-side portion 67bs of a blower 67b.

DESCRIPTION OF EMBODIMENTS

Figure 1A:
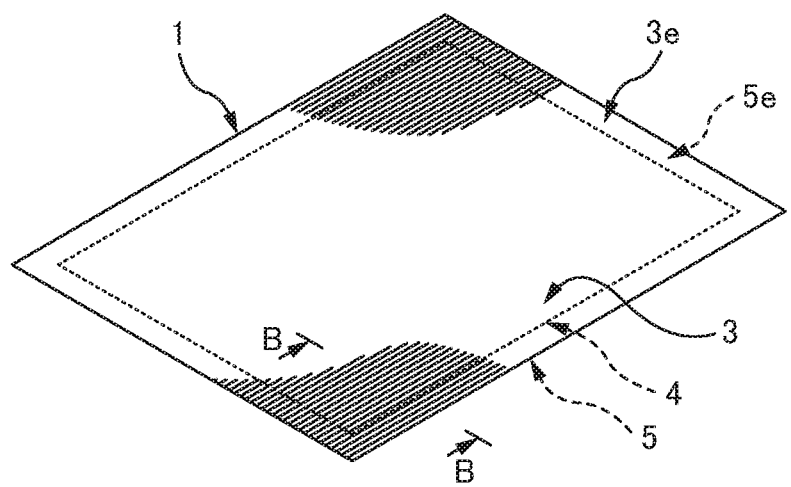
FIG. 1A is an exterior perspective view of a pet sheet 1 as an example of an absorbent article.

At least the following examples will become evident from the description of this specification and the accompanying drawings.

A manufacturing apparatus of a sheet-like member of an absorbent article to manufacture the sheet-like member by joining a non-woven fabric to another member of the absorbent article, the manufacturing apparatus including:
 a bulk restoring device that restores bulk of the non-woven fabric through heating the non-woven fabric by blowing hot wind onto the non-woven fabric while conveying the non-woven fabric along a conveying direction, the non-woven fabric being continuous in the conveying direction; and
 a joining device that joins the non-woven fabric whose bulk has been restored with the hot wind to the other member using an adhesive, the non-woven fabric being at a higher temperature than a temperature before being heated with the hot wind.

According to this manufacturing apparatus of a sheet-like member of an absorbent article, the temperature of the non-woven fabric at the time of being joined to the other member with the joining device is a higher temperature than the temperature before being heated with the hot wind, and therefore the adhesive that joins the non-woven fabric and the other member has a low viscosity and is in a high fluidity state. Accordingly, the impregnation and permeation of the adhesive into the non-woven fabric proceeds smoothly at least during joining, and the adhered area is expanded, and consequently the adhesion strength between the non-woven fabric and the other member can be raised.

Also, since the adhesion strength can be raised as described above, there is no need for the sheet-like member formed by the joining of the non-woven fabric and the other member to be heavily pressed in the thickness direction after the joining device for the purpose of raising the adhesion strength, and consequently the non-woven fabric in the sheet-like member can be substantially kept in a state of having the bulk that was restored with the bulk restoring device.

In the above manufacturing apparatus of a sheet-like member of an absorbent article,
 it is preferable that the bulk restoring device has a case member provided with an inlet for the non-woven fabric and an outlet for the non-woven fabric,
 one of an inlet-side portion and an outlet-side portion of the case member has a blast opening that blasts the hot wind into a space inside the case member toward another one of the inlet-side portion and the outlet-side portion, and
 the other one of the inlet-side portion and the outlet-side portion has a discharge port that discharges, from the case member, the hot wind that has flowed while being in contact with one surface of both surfaces of the non-woven fabric.

According to this manufacturing apparatus of a sheet-like member of an absorbent article, hot wind is blasted from the blast opening so as to flow from one side to the other side in the conveying direction, and as the hot wind flows from the one side to the other side, the hot wind heats the non-woven fabric while being in contact with one of the two surfaces of the non-woven fabric. Accordingly, the bulk of the non-woven fabric can be reliably restored.

Also, because the hot wind flows over the surface of the non-woven fabric, compression of the non-woven fabric in the thickness direction is effectively prevented. It is therefore possible to smoothly perform bulk restoration.

In the above manufacturing apparatus of a sheet-like member of an absorbent article,
 it is preferable that the bulk restoring device has a cooling device that cools the non-woven fabric that has been heated with the hot wind, before the non-woven fabric is joined to the other member, and
 the cooling device cools the non-woven fabric with a higher temperature than a temperature before the non-woven fabric is heated as a lower limit value of the temperature of the non-woven fabric.

According to this manufacturing apparatus of a sheet-like member of an absorbent article, the cooling device cools the non-woven fabric that was heated with the hot wind. Accordingly, it is possible to effectively suppress a phenomenon that can occur due to the temperature of the non-woven fabric being high after being heated with the hot wind, that is, a phenomenon in which the width direction dimensions vary due to softening of the non-woven fabric.

Also, the cooling device cools the non-woven fabric with the lower limit value of the temperature of the non-woven fabric, which is a higher temperature than the temperature before being heated. Accordingly, even in the cooled non-woven fabric, the adhesive can have a low viscosity and be kept in a high fluidity state, and consequently the adhesive can be caused to impregnate and permeate the non-woven fabric.

In the above manufacturing apparatus of a sheet-like member of an absorbent article, it is preferable that the cooling device has a case member provided with an inlet for the non-woven fabric and an outlet for the non-woven fabric, one of an inlet-side portion and an outlet-side portion of the case member has a blast opening that blasts cooling wind into a space inside the case member toward another one of the inlet-side portion and the outlet-side portion, and the other one of the inlet-side portion and the outlet-side portion has a discharge port that discharges, from the case member, the wind that has flowed while being in contact with one surface of both surfaces of the non-woven fabric.

According to this manufacturing apparatus of a sheet-like member of an absorbent article, cooling wind is blasted from the one blast opening so as to flow from one side to the other side in the conveying direction, and the cooling wind cools the non-woven fabric while being in contact with one of both surfaces of the non-woven fabric as it flows from the one side to the other side. Accordingly, the non-woven fabric can be reliably cooled.

Also, because the cooling wind flows over the surface of the non-woven fabric, compression of the non-woven fabric in the thickness direction is effectively prevented. Accordingly, the loss of the restored bulk with the cooling wind can be reliably avoided.

In the above manufacturing apparatus of a sheet-like member of an absorbent article, it is preferable that the adhesive is a thermoplastic adhesive, and the adhesive is applied to at least the non-woven fabric.

According to this manufacturing apparatus of a sheet-like member of an absorbent article, a thermoplastic adhesive is used as the adhesive, and therefore the introduction of heat reduces the viscosity of the adhesive and raises its fluidity, and consequently the adhesive reliably impregnates and permeates the non-woven fabric. Accordingly, it is possible to reliably raise the adhesion strength between the non-woven fabric and the other member.

Also, the adhesive is applied to at least the non-woven fabric, thus making it possible to ensure sufficient time for the impregnation and permeation of the adhesive into the non-woven fabric.

In the above manufacturing apparatus of a sheet-like member of an absorbent article, it is preferable that the bulk restoring device has a heating unit that blows hot wind onto the non-woven fabric, the heating unit is arranged directly above a conveying route along which the other member is conveyed, and the non-woven fabric that has been heated with the heating unit merges into the conveying route for the other member in the joining device.

According to this manufacturing apparatus of a sheet-like member of an absorbent article, the heating unit is arranged directly above the conveying route for the other member, and therefore the heated non-woven fabric can be swiftly merged into the conveying route for the other member in a relatively short time after being heated. Accordingly, it is possible to join the non-woven fabric to the other member with the temperature of the non-woven fabric in a high state.

In the above manufacturing apparatus of a sheet-like member of an absorbent article, it is preferable that the conveying route for the non-woven fabric in the heating unit is oriented along a horizontal direction.

According to this manufacturing apparatus of a sheet-like member of an absorbent article, the height dimension of the heating unit in the vertical direction can be reduced. Accordingly, it is possible to prevent problems in advance that can occur due to the heating unit being arranged directly above the other member. For example, in the case where the height dimension of the heating unit in the vertical direction is large, it tends to interfere with existing installed objects such as a duct located above the manufacturing line, and according to the above configuration, it is possible to reduce the height dimension of the heating unit, thus making it possible to prevent in advance interference with existing installed objects above it.

In the above manufacturing apparatus of a sheet-like member of an absorbent article, it is preferable that the joining device has a pair of rolls that rotate with outer circumferential surfaces of the rolls opposing each other, and when the non-woven fabric and the other member are passed between the pair of rolls in a state laid on each other, the non-woven fabric and the other member are joined with the adhesive due to being clamped with the pair of rolls.

According to this manufacturing apparatus of a sheet-like member of an absorbent article, the joining device can be realized with the simple configuration of a pair of rolls that rotate.

In the above manufacturing apparatus of a sheet-like member of an absorbent article, it is preferable that the apparatus includes:

an adhesive application device that applies the adhesive to at least one of the other member and the non-woven fabric whose bulk has been restored with the bulk restoring device.

This manufacturing apparatus of a sheet-like member of an absorbent article has an adhesive application device, thus making it possible to reliably apply the adhesive for joining the non-woven fabric and the other member.

In the above manufacturing apparatus of a sheet-like member of an absorbent article, it is preferable that the adhesive application device applies the adhesive to the non-woven fabric in a position on a downstream side of the bulk restoring device in the conveying direction.

According to this manufacturing apparatus of a sheet-like member of an absorbent article, the adhesive is applied to the non-woven fabric after hot wind has been blown thereon with the bulk restoring device. This effectively avoids the case where the adhesive applied to the non-woven fabric in a predetermined application pattern is disturbed with the hot wind, thus making it possible to join the non-woven fabric and the other member with a predetermined application pattern that has been determined in advance. This also contributes to an improvement in adhesion strength.

Also, a manufacturing method of a sheet-like member of an absorbent article to manufacture the sheet-like member by joining a non-woven fabric to another member of the absorbent article is the manufacturing method including:

restoring bulk of the non-woven fabric through heating the non-woven fabric by blowing hot wind onto the non-woven fabric while conveying the non-woven fabric along a conveying direction, the non-woven fabric being continuous in the conveying direction; and joining the non-woven fabric whose bulk has been restored with the hot wind to the other member using an adhesive, the non-woven fabric being at a higher temperature than a temperature before being heated with the hot wind.

According to this manufacturing method of a sheet-like member of an absorbent article, the temperature of the non-woven fabric at the time of being joined to the other member is a higher temperature than the temperature before being heated with the hot wind, and thus the adhesive that joins the non-woven fabric and the other member has a low viscosity and is in a high fluidity state. Accordingly, the impregnation and permeation of the adhesive into the non-woven fabric proceeds smoothly at least during joining, and consequently it is possible to raise the adhesion strength between the non-woven fabric and the other member.

Also, since the adhesion strength can be raised as described above, there is no need for the sheet-like member formed by the joining of the non-woven fabric and the other member to be heavily pressed in the thickness direction after the joining for the purpose of raising the adhesion strength, and consequently the non-woven fabric in the sheet-like member can be substantially kept in a state of having the bulk that has been restored with the hot wind.

Embodiments

A manufacturing apparatus 11 for manufacturing a sheet-like member of an absorbent article of an embodiment is used in a manufacturing line for a pet sheet 1 as an example of an absorbent article.

Figure 1B:
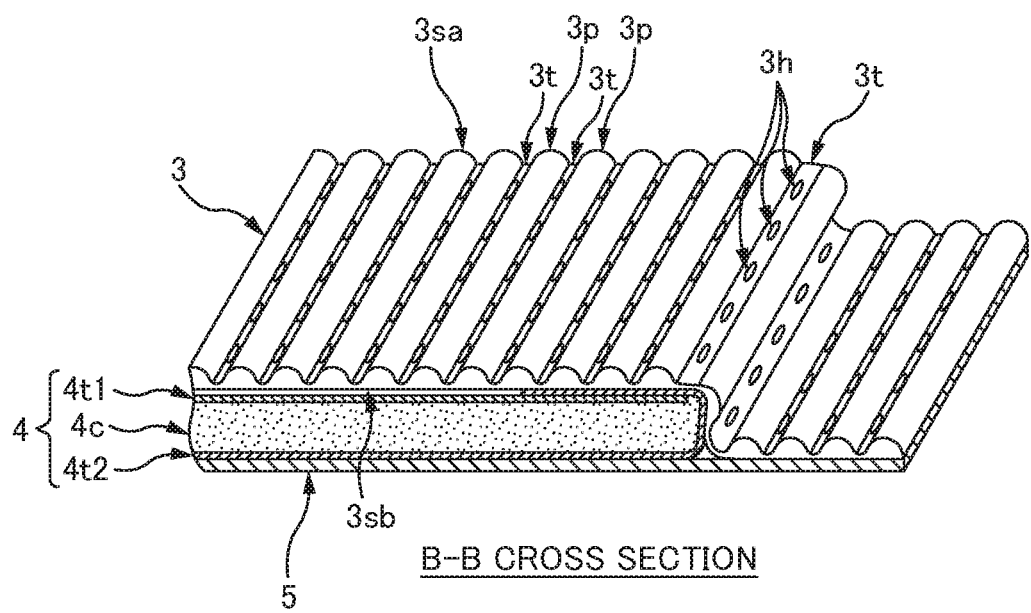
FIG. 1B is an enlarged perspective view of the case of cutting the pet sheet 1 along line B-B in FIG. 1A.

FIG. 1A is an exterior perspective view of the pet sheet 1, and FIG. 1B is an enlarged perspective view of the case of cutting the pet sheet 1 along line B-B in FIG. 1A.

The pet sheet 1 is used in the treatment of excretion from animals such as dogs or cats, and is used in the state of being placed on the floor or the like as shown in FIG. 1A. The pet sheet 1 has, for example, a liquid-permeable top sheet 3 that is rectangular in a plan view, a liquid-impermeable back sheet 5 that has roughly the same shape, and a liquid-absorbent absorbent body 4 interposed between the sheets 3 and 5. The absorbent body 4 is joined to both the top sheet 3 and the back sheet 5 using a hot-melt adhesive, and the portions of the top sheet 3 and the back sheet 5 that protrude laterally beyond the absorbent body 4, that is to say peripheral edge portions 3e and 5e of the sheets 3 and 5, are joined together using the hot-melt adhesive.

Incidentally, the hot-melt adhesive referred to here is a thermoplastic adhesive that can be melted by heat and applied in a fluidized state. Examples of such a hot-melt adhesive include an olefin-based hot-melt adhesive and a styrene-based hot-melt adhesive, but other types may be used.

As shown in FIG. 1B, the absorbent body 4 has an absorbent core 4c, which is formed by laminating liquid-absorbent fibers such as pulp fibers and superabsorbent polymers (so-called SAP) in an approximately rectangular shape in a plan view, as well as a covering sheet that covers the core 4c, for example. The covering sheet is a liquid-permeable sheet made of tissue paper or the like, for example, and in this example, two covering sheets 4t1 and 4t2 are provided. More specifically, the core is covered with the one covering sheet 4t1 on the skin-side surface, and covered with the other covering sheet 4t2 on the non-skin-side surface. Both the skin-side surface and the non-skin-side surface may be covered by one covering sheet, however, and in some cases the covering sheets 4t1 and 4t2 need not be provided.

The back sheet 5 is a film member made of, for example, polyethylene (hereinafter, PE), polypropylene (hereinafter, PP), polyethylene terephthalate (hereinafter, PET), or the like. There is no limitation whatsoever to the above examples, however, and any liquid-impermeable sheet can be used.

The top sheet 3 is made of the non-woven fabric 3. In this example, of two surfaces 3sa and 3sb of the non-woven fabric 3, the one surface 3sb is an approximately flat surface, whereas the other surface 3sa has a wavy shape. Specifically, the surface 3sa is made up of straight line-shaped groove portions 3t and straight line-shaped projection portions 3p that are formed alternatingly. The projection portions 3p are formed by applying a known air stream blowing process (see JP 2009-11179A, for example) such that fibers that were originally in the groove portion 3t regions are blown together so as to pile up, thus forming a sparse state with large fiber intervals. Accordingly, the non-woven fabric 3 is bulky overall. Also, multiple through-holes 3h, 3h . . . that penetrate in the thickness direction may be formed in the groove portions 3t, and these through-holes are provided in this example.

The average basis weight of the non-woven fabric 3 is 10 to 200 (g/m$^2$) for example, the average basis weight of the central portion in the projection portions 3p is 15 to 250 (g/m$^2$) for example, and the average basis weight of the bottom portion in the groove portions 3t is 3 to 150 (g/m$^2$) for example.

Also, it is preferable that the fibers of the non-woven fabric 3 are composite fibers having a core-in-sheath structure with a PET core and a PE sheath, but other thermoplastic resin fibers may be used. For example, composite fibers having a core-in-sheath structure with a PP core and a PE sheath may be used, fibers with a side-by-side structure, or single-component fibers made up of solely a thermoplastic resin may be used.

Furthermore, the non-woven fabric 3 may have crimped fibers. Note that crimped fibers are fibers having a crimped shape, such as a zigzag shape, an Ω shape, a spiral shape, or the like.

Also, the fiber length of the fibers included in the non-woven fabric 3 is selected from the range of 20 to 100 mm for example, and the fiber density is selected from the range of 1.1 to 8.8 (dtex).

The pet sheet 1 is manufactured in a pet sheet 1 manufacturing line. In this manufacturing line, the sheet-like member manufacturing apparatus 11 of this embodiment manufactures a continuous body 1a of pet sheets 1 as one example of a sheet-like member. Specifically, a non-woven fabric 3a that is to be the top sheet 3a and is continuous in the conveying direction, multiple absorbent bodies 4, 4 . . . lined up in the conveying direction, and a back sheet 5a that is continuous in the conveying direction are stacked in the thickness direction and joined using the hot-melt adhesive, thus manufacturing a continuous body 1a of pet sheets 1 in which multiple pet sheets 1, 1 . . . are continuous in the conveying direction.

Figure 2:
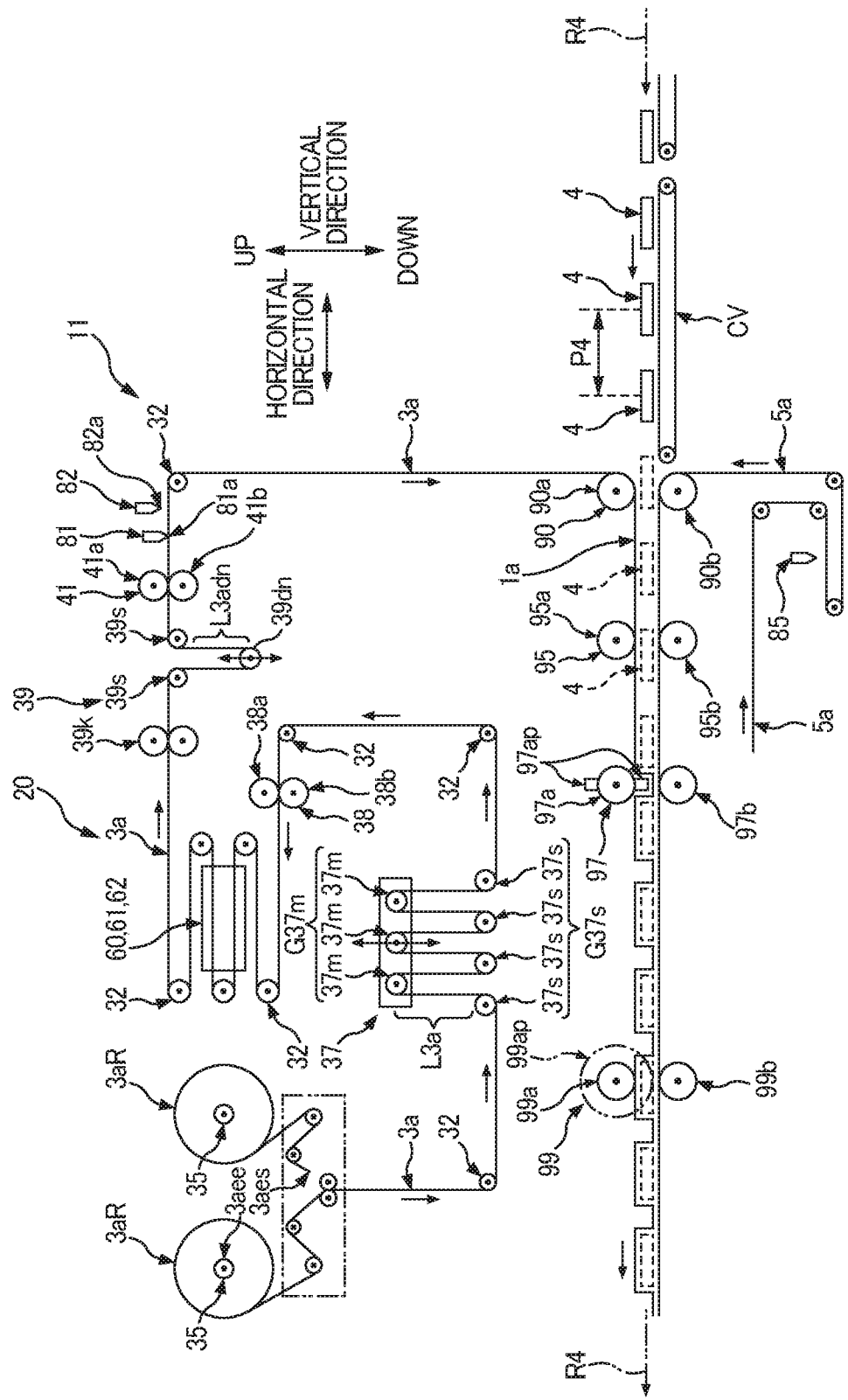
FIG. 2 is a schematic side view of a bulk restoring device 20 according to an embodiment.

Here, the non-woven fabric 3a that is to be the top sheet 3a is carried to the manufacturing apparatus 11 in the form of a non-woven fabric whole cloth 3aR (FIG. 2). Specifically, the non-woven fabric 3a having the above-described projection portions 3p is stored in a state of having been wound into a roll, and the non-woven fabric whole cloth 3aR is then carried from the storage location to the manufacturing apparatus 11. The non-woven fabric 3a is then fed from the non-woven fabric whole cloth 3aR as the top sheet 3a material in the manufacturing apparatus 11. As previously described, however, there is a risk of the non-woven fabric 3a losing bulk in the non-woven fabric whole cloth 3aR.

For this reason, the lost bulk of the non-woven fabric 3a is first restored in the manufacturing apparatus 11, and then the non-woven fabric 3a is joined to the absorbent body 4 and the back sheet 5a. Specifically, the manufacturing apparatus 11 has the bulk restoring device 20 and a joining device 90. First, the bulk restoring device 20 feeds the non-woven fabric 3a from the non-woven fabric whole cloth 3aR and conveys it in the conveying direction while also blowing hot wind onto the non-woven fabric 3a so as to heat it, thus restoring the bulk of the non-woven fabric 3a. The heated non-woven fabric 3a is then conveyed to a merging position for merging with the absorbent bodies 4, 4 . . . and the back sheet 5a. The joining device 90 is arranged at the merging position, and when the non-woven fabric 3a passes through the joining device 90, the non-woven fabric 3a is stacked onto the absorbent bodies 4, 4 . . . and the back sheet 5a and joined thereto with the joining device 90. This results in the production of the continuous body 1a of pet sheets 1 in which multiple pet sheets 1, 1 . . . are continuous in the conveying direction.

Incidentally, in the present embodiment, at any point in time between the end of heating with the bulk restoring device 20 and the arrival of the non-woven fabric 3a at the joining device 90, the hot-melt adhesive for the above-described joining is applied to the non-woven fabric 3a by adhesive application devices 81 and 82. Also, during joining with the joining device 90, a sufficient amount of heat remains from the heating performed with the bulk restoring device 20, and thus the temperature of the non-woven fabric 3a during this joining is a higher temperature than before being heated with the bulk restoring device 20.

Accordingly, even in the state of being applied to the non-woven fabric 3a, the hot-melt adhesive has a sufficiently low viscosity and is in a high fluidity state. For this reason, the impregnation and permeation of the adhesive into the non-woven fabric 3a during joining proceeds smoothly, and the non-woven fabric 3a is joined to the absorbent bodies 4, 4 . . . and the back sheet 5a with a high adhesion strength. As a result, it is possible to reduce the press processing that is performed thereafter with a pressing device 95 for the purpose of increasing the adhesion strength, thus making it possible to substantially keep the non-woven fabric 3a in a bulky state even when in the form of the continuous body 1a of pet sheets 1 in which the non-woven fabric 3a has been joined to both the absorbent bodies 4, 4 . . . and the back sheet 5a.

Incidentally, in the example shown in FIG. 2, the hot-melt adhesive is applied to the back sheet 5a as well with the adhesive application device 85 at a point in time before the above-described joining. The back sheet 5a and the absorbent bodies 4, 4 . . . are firmly joined with this adhesive.

The following describes the bulk restoring device 20, the adhesive application devices 81 and 82, and the joining device 90 included in the manufacturing apparatus 11 of this embodiment. Note that the bulk restoring device 20, the adhesive application devices 81 and 82, and the joining device 90 are arranged in the manufacturing line and supported by an appropriate support member (not shown) of the manufacturing line. In this example, a so-called panel board (not shown) is used as an example of the support member. This panel board is a plate member erected vertically on the floor portion of the manufacturing line and has a vertical surface (surface whose normal direction is oriented in the horizontal direction), and the devices 20, 81, 82, 90, . . . and so on are supported on the vertical surface in a cantilevered state, for example. Hereinafter, the normal direction of the vertical surface will be referred to as the "CD direction". In FIG. 2, the CD direction is oriented in a direction penetrating the paper surface of FIG. 2, and more specifically, the CD direction is oriented in a direction penetrating the paper surface of FIG. 2 among any of the directions in the horizontal plane. Also, the non-woven fabric 3a and the back sheet 5a are basically conveyed in an orientation in which the width directions of the non-woven fabric 3a and the back sheet 5a are oriented in the CD direction, and therefore the conveying direction of the non-woven fabric 3a and the back sheet 5a is oriented in any direction that is orthogonal to the CD direction. Note that the aforementioned support member is not limited in any way to being a panel board, and other support members may be used.

Bulk Restoring Device 20

As shown in FIG. 2, the bulk restoring device 20 has a conveying portion 30 that feeds the non-woven fabric 3a from the non-woven fabric whole cloth 3aR and conveys it along a predetermined conveying route, and a heating portion 60 that heats the non-woven fabric 3a at a predetermined location along the conveying route. The non-woven fabric 3a with restored bulk due to being heated with the heating portion 60 is then sent downstream in the conveying direction, the hot-melt adhesive is applied thereto with the adhesive application devices 81 and 82 at the downstream side position, and then the non-woven fabric 3a is sent to the previously-described joining device 90 located further downstream.

(1) Conveying Portion 30

The conveying portion 30 has multiple conveying rollers 32 that define the conveying route for the non-woven fabric 3a. The conveying rollers 32, 32 . . . are supported rotatably about rotation shafts oriented in the CD direction, and therefore the non-woven fabric 3a is conveyed in an orientation in which the width direction thereof is oriented in the CD direction. The conveying rollers 32, 32 . . . are basically driven rollers that rotate passively (i.e., rollers that rotate upon receiving rotation force from contact with the non-woven fabric 3a being conveyed).

On the upstream side of the heating unit 61 of the heating portion 60 in the conveying direction, the conveying portion 30 also has feeding devices 35, 35, a material joining device 36, an accumulator device 37, and an upstream pinch roll device 38 lined up in the stated order from upstream to downstream in the conveying direction. On the downstream side of the heating unit 61 in the conveying direction, the conveying portion 30 further has a tension control device 39 and a downstream pinch roll device 41 lined up in the stated order from upstream to downstream in the conveying direction.

Each of the feeding devices 35 is a device for feeding the non-woven fabric 3a from the non-woven fabric whole cloth 3aR, and has a rotation shaft oriented in the CD direction. The non-woven fabric whole cloth 3aR is supported rotatably about the rotation shaft. The rotation shaft is driven to rotate by a servo motor (not shown) serving as a drive source for example, and thus feeds the non-woven fabric 3a from the non-woven fabric whole cloth 3aR. Note that the servo motor performs the feeding operation in coordination with the accumulator device 37. This coordination will be described later.

In this example, two feeding devices 35, 35 are provided. Basically, they are switched between each other and used alternatingly. Specifically, in this configuration, while one of the feeding devices 35 is feeding the non-woven fabric 3a, the other feeding device 35 is in the standby state, and then when the non-woven fabric whole cloth 3aR is used up from the one feeding device 35, the feeding device 35 in the standby state begins to feed the non-woven fabric 3a. These feeding devices 35 are well known, and thus will not be described in detail.

The material joining device 36 is a device for, at a time somewhat before the operating feeding device 35 completes the feeding of all of the non-woven fabric 3a from the non-woven fabric whole cloth 3aR, joining a trailing end portion 3aee of the non-woven fabric 3a of that whole cloth 3aR to a leading end portion 3aes of the non-woven fabric 3a of the non-woven fabric whole cloth 3aR attached to the standby feeding device 35. Accordingly, it is possible to continuously feed the non-woven fabric 3a without interruption. This material joining device 36 is also well known, and thus will not be described in detail.

The accumulator device 37 is a device for accumulating the non-woven fabric 3a fed from the feeding device 35 so as to be able to be dispensed downstream in the conveying direction. In the case where the non-woven fabric 3a is not fed from the feeding device 35, such as when joining processing is performed with the material joining device 36, the accumulator device 37 itself dispenses the non-woven fabric 3a accumulated therein downstream, thus preventing downstream processing from being influenced by the pause in feeding from the feeding device 35. Note that the non-woven fabric 3a is fed from the feeding device 35 with a faster velocity value (m/min) than the conveying velocity value (m/min) of the non-woven fabric 3a at a position immediately downstream of the accumulator device 37, from when the pause in feeding from the feeding device 35 ends until when a specified accumulation amount is reached, and thus the accumulator device 37 accumulates an amount of the non-woven fabric 3a equal to the amount that was dispensed during the pause in feeding.

In this example, the accumulator device 37 has a fixed roller group G37s made up of multiple rollers 37s, 37s . . . that are fixed at fixed positions, and a movable roller group G37m made up of multiple rollers 37m, 37m . . . provided so as to be capable of moving back and forth in the vertical direction. The non-woven fabric 3a is alternatingly wound around the rollers 37s that belong to the fixed roller group G37s and the rollers 37m that belong to the movable roller group G37m, thus forming loops L3a in the non-woven fabric 3a and accumulating the non-woven fabric 3a.

Here, the movable roller group G37m moves back and forth in the vertical direction in accordance with the magnitude of tension (N) in the non-woven fabric 3a. Specifically, in the case where the magnitude of the tension in the non-woven fabric 3a is larger than a tension setting value (N) that has been set in advance, the movable roller group G37m moves such that the loops L3a decrease in size, and thus the accumulated non-woven fabric 3a is dispensed and supplied downstream. In the case where the magnitude of the tension in the non-woven fabric 3a is smaller than the setting value, the movable roller group G37m moves such that the loops L3a increase in size, thus accumulating the non-woven fabric 3a. Accordingly, at a position immediately downstream from the accumulator device 37, the magnitude of the tension in the non-woven fabric 3a is substantially maintained at the setting value, and in this sense, the accumulator device 37 also exhibits a function similar to that of the later-described tension control device 39. The accumulator device 37 is also well known, and thus will not be described in further detail.

The upstream pinch roll device 38 is a device for feeding the non-woven fabric 3a to the heating unit 61 of the heating portion 60. Specifically, the upstream pinch roll device 38 has a pair of rolls 38a and 38b arranged such that their outer circumferential surfaces oppose each other, and at least either the roll 38a or the roll 38b is a driving roll 38a (38b) that is driven to rotate by a servo motor (not shown) that serves as a drive source. The non-woven fabric 3a is fed to the heating unit 61 by this driving rotation.

The driving roll 38a (38b) is driven to rotate in coordination with a driving roll 39k of the tension control device 39 located on the downstream side of the heating unit 61 in the conveying direction. For example, the driving roll 38a (38b) of the pinch roll device 38 is driven to rotate so as to maintain a constant ratio R between a rotation speed value V39k of the driving roll 39k of the tension control device 39 and a rotation speed value V38a (V38b) of the driving roll 38a (38b) of the pinch roll device 38. The ratio R is set to any value from 0.9 to 1.1, for example.

The tension control device 39 is arranged on the downstream side of the heating unit 61 in the conveying direction. Also, the tension control device 39 adjusts the tension such that the magnitude of the tension (N) in the non-woven fabric 3a at a position immediately downstream of the device 39 is a predetermined target value (N).

The tension control device 39 is constituted using a so-called dancer roll 39dn. Specifically, the tension control device 39 has a pair of fixed rolls 39s, 39s that are fixed at fixed positions with a gap between each other in the conveying direction, the dancer roll 39dn that is provided at a position between the pair of fixed rolls 39s, 39s and is provided so as to be capable of moving back and forth in a direction orthogonal to the CD direction, and a driving roll 39k that is provided on the upstream side of the dancer roll 39dn in the conveying direction. The non-woven fabric 3a is wound around all three of the pair of fixed rolls 39s, 39s, the dancer roll 39dn, and the driving roll 39k, and a loop L3adn is formed in the non-woven fabric 3a wound around the pair of fixed rolls 39s, 39s and the dancer roll 39dn. Force corresponding to twice the target value of the tension in the non-woven fabric 3a is applied to the dancer roll 39dn in the direction for increasing the size of the loop L3adn of the back and forth moving directions . Accordingly, in the case where the magnitude of the tension in the non-woven fabric 3a is larger than the target value, the dancer roll 39dn moves such that the loop L3adn decreases in size, whereas in the case where the magnitude of the tension in the non-woven fabric 3a is smaller than the target value, the dancer roll 39dn moves such that the loop L3adn increases in size. Meanwhile, the driving roll 39k is driven to rotate by a servo motor (not shown), and this motor rotates the driving roll 39k and feeds the non-woven fabric 3a such that the size of the loop L3adn is a predetermined value. For example, in the case where the size is larger than the predetermined value, the rotation speed value (m/min) of the driving roll 39k is reduced, whereas in the case where the size is smaller than the predetermined value, the rotation speed value of the driving roll 39k is increased. Accordingly, the magnitude of the tension in the non-woven fabric 3a at a position immediately downstream of the tension control device 39 is adjusted so as to be the target value.

The downstream pinch roll device 41 is a device for feeding the non-woven fabric 3a to the joining device 90. Specifically, the downstream pinch roll device 41 has a pair of rolls 41a and 41b arranged such that their outer circumferential surfaces oppose each other, and at least either the roll 41a or the roll 41b is a driving roll 41a (41b) that is driven to rotate by a servo motor (not shown) that serves as a drive source. The non-woven fabric 3a is fed to the joining device 90 with this driving rotation. The driving roll 41a (41b) is driven to rotate in coordination with the joining device 90. For example, the driving roll 41*a* (41*b*) of the downstream pinch roll device 41 is driven to rotate such that the rotation speed value of rolls 90*a* and 90*b* included in the joining device 90 and the rotation speed value of the driving roll 41*a* (41*b*) of the downstream pinch roll device 41 are approximately the same value.

(2) Heating Portion 60

Figure 3A:
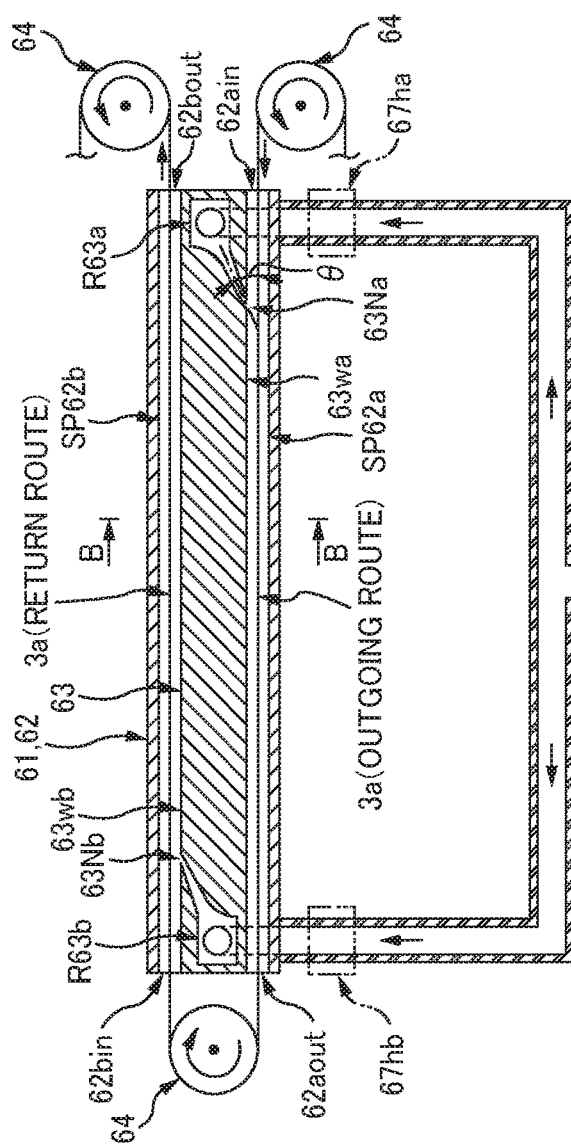
FIG. 3A is an explanatory diagram of a heating portion 60 that makes up a main portion of the bulk restoring device 20.
Figure 3B:
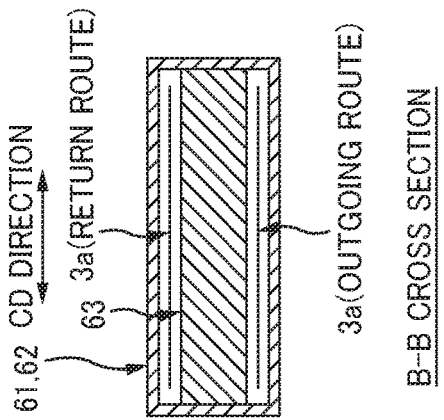
FIG. 3B is a cross-sectional diagram taken along line B-B in FIG. 3A.

FIG. 3A is a schematic side view of the heating portion 60, and FIG. 3B is a cross-sectional view taken along B-B in FIG. 3A. In FIG. 3A, the heating unit 61 making up the main portion of the heating portion 60 is shown in a cross-sectional view.

As shown in FIG. 3A, the heating portion 60 has the heating unit 61 that heats the non-woven fabric 3*a* by blowing hot wind onto the non-woven fabric 3*a* while passing it through the interior, and a hot wind supplying device 67 that supplies hot wind to the heating unit 61.

The heating unit 61 has a case member 62 that is open in the two end portions in the lengthwise direction, and multiple guide rollers 64, 64, 64 . . . that are provided outside the case member 62 and guide the non-woven fabric 3*a* so as to move back and forth inside the case member 62. A straight outgoing path and return path in the conveying route for the non-woven fabric 3*a* are formed inside the case member 62 with the guide rollers 64, 64, 64.

As shown in FIG. 3A, the case member 62 has a partition member 63 inside, and the partition member 63 divides the space inside the case member 62 into an outgoing route space SP62*a* and a return route space SP62*b*. Specifically, the outgoing route space SP62*a* and the return route space SP62*b* are separated such that air cannot travel between the spaces. Due to the separation with the partition member 63, both an outgoing route inlet 62*a*in and a return route outlet 62*b*out for the non-woven fabric 3*a* are formed in one of the both end portions of the case member 62 in the lengthwise direction, and both an outgoing route outlet 62*a*out and a return route inlet 62*b*in for the non-woven fabric 3*a* are formed in the other end portion.

Furthermore, of both wall surfaces 63*wa* and 63*wb* of the partition member 63, the wall surface 63*wa* adjacent to the outgoing route space SP62*a* (also referred to hereinafter as the outgoing route wall surface 63*wa*), and of the two wall surfaces 63*wa* and 63*wb* of the partition member 63, the wall surface 63*wb* adjacent to the return route space SP62*b* (also referred to hereinafter as the return route wall surface 63*wb*) are each provided parallel with the conveying direction and the CD direction, and thus the outgoing route wall surface 63*wa* and the return route wall surface 63*wb* are each approximately parallel with the surfaces of the non-woven fabric 3*a*. A blast opening 63Na shaped as a slit elongated in the CD direction is provided in a portion of the outgoing route wall surface 63*wa* on the upstream side in the outgoing route (this corresponds to the "inlet-side portion of the case member"), and a blast opening 63Nb shaped as a slit elongated in the CD direction is also provided in a portion of the return route wall surface 63*wb* on the upstream side in the return route (this corresponds to the "inlet-side portion of the case member").

More specifically, the partition member 63 has pressure chambers R63*a* and R63*b* inside in correspondence with the aforementioned portions. Hot wind is supplied from the hot wind supplying device 67 into the pressure chambers R63*a* and R63*b*. The pressure chambers R63*a* and R63*b* each have a cross-sectional shape (shape of the cross-section whose normal direction is the CD direction) that is a tapered shape of roughly becoming increasingly narrow toward the downstream side in the conveying direction, and are each in communication with the corresponding outgoing route space SP62*a* and return route space SP62*b* in the tip portions of the tapered shape. Accordingly, the tip portions function as the blast openings 63Na and 63Nb. According to such blast openings 63Na and 63Nb, hot wind is blasted toward one surface of the both surfaces of the non-woven fabric 3*a*, while also being blasted toward the downstream side in the conveying direction with an acute angle of inclination θ relative to the surface of the non-woven fabric 3*a*.

Accordingly, the hot wind blasted from the outgoing route blast opening 63Na comes into contact with the surface of the non-woven fabric 3*a* with a velocity component in a direction toward the downstream side in the conveying direction, continues to flow over the surface as is, and is then discharged to the outside through the outlet 62*a*out (corresponding to the discharge port) located the most downstream in the conveying direction in the outgoing route space SP62*a*. The hot wind blasted from the return route blast opening 63Nb comes into contact with the surface of the non-woven fabric 3*a* with a velocity component in a direction toward the downstream side in the conveying direction, continues to flow over the surface as is, and is then discharged to the outside through the outlet 62*b*out (corresponding to the discharge port) located the most downstream in the conveying direction in the return route space SP62*b*.

The hot wind flows over the surface of the non-woven fabric 3*a* in this way, thus effectively avoiding a situation in which the hot wind compresses the non-woven fabric 3*a* in the thickness direction of the non-woven fabric 3*a*, thus making it possible to smoothly perform bulk restoration.

By adjusting the hot wind flow rate ($m^3$/min), a hot wind wind velocity value Vw (m/min) can be set higher than the conveying velocity value V3 (m/min) of the non-woven fabric 3*a*. Accordingly, the hot wind blasted from the blast openings 63Na and 63Nb passes over the non-woven fabric 3*a* in a manner of sliding over the surface of the non-woven fabric 3*a*, and ultimately is discharged to the outside through the outlets 62*a*out and 62*b*out.

Accordingly, the hot wind can be reliably put in a turbulent state based on the relative velocity difference between the hot wind and the non-woven fabric 3*a*. As a result, the heat transfer efficiency is dramatically improved, the non-woven fabric 3*a* can be efficiently heated, and the bulk is swiftly restored. The fibers in the non-woven fabric 3*a* are randomly loosened with the hot wind in a turbulent state, and the bulk restoration is promoted by this as well.

It should be noted that the wind velocity value Vw (m/min) of the hot wind is a value obtained by the flow rate ($m^3$/min) of hot wind supplied to the outgoing route space SP62*a* or the return route space SP62*b* being divided by the cross-sectional area of the outgoing route space SP62*a* or the return route space SP62*b* (i.e., the area of a cross-section whose normal direction is the conveying direction), for example.

Preferably the magnitude relationship between the wind velocity value Vw and the conveying velocity value V3 described above is established over the entire length of the outgoing route space SP62*a* and the return route space SP62*b* in the conveying direction, but it is not necessarily required to be established over the entire length. Specifically, as long as the magnitude relationship is established in even a portion of the spaces SP62*a* and SP62*b*, the above-described actions and effects related to the turbulent state can be properly obtained.

Note that the shapes of the outgoing route and return route blast openings 63Na and 63Nb are each a rectangle whose lengthwise direction is oriented in the CD direction. Also, the CD-direction dimension of the outgoing route blast opening 63Na is assumed to be the same as the CD-direction dimension of the outgoing route space SP62a, and the CD-direction dimension of the return route blast opening 63Nb is assumed to be the same as the CD-direction dimensions of the return route space SP62b, but there is no limitation whatsoever to this. For example, the blast openings 63Na and 63Nb may be smaller. Preferably the CD-direction dimension of the blast openings 63Na and 63Nb is larger than the width-direction dimension of the non-woven fabric 3a (CD-direction dimension), and this configuration suppresses heating irregularity in the CD direction.

The widthwise-direction dimension of the blast openings 63Na and 63Nb (dimension in the direction orthogonal to the lengthwise direction) is selected and set to any value in the range of 1 mm to 10 mm, for example.

Furthermore, preferably the angle θ that the hot wind blast direction forms with the conveying direction of the non-woven fabric 3a in the positions of the blast openings 63Na and 63Nb falls within the range of 0° to 30°, and it is further preferable that this angle θ falls within the range of 0° to 10° (FIG. 3A). According to this configuration, it is possible to cause the hot wind to reliably flow along the surface of the non-woven fabric 3a.

It should be noted that in the example in FIG. 2, the heating unit 61 is of the horizontal type in which the lengthwise direction of the case member 62 is oriented in the horizontal direction, and therefore the outgoing route and return route in the conveying route of the non-woven fabric 3a are horizontal, but there is no limitation whatsoever to this. In other words, depending on the case, a vertical type may be used. Specifically, a configuration is possible in which the lengthwise direction of the case member 62 is oriented in the vertical direction, and thus the outgoing route and return route in the conveying route of the non-woven fabric 3a are vertical. Note that this vertical type is superior in that only a small amount of planar space is required for the installation of the heating unit 61. Furthermore, depending on the layout circumstances, the heating unit 61 may be arranged with the lengthwise direction of the case member 62 inclined from both the vertical direction and the horizontal direction.

As shown in FIG. 3A, the hot wind supplying device 67 has a blower 67b and a heater 67h. The wind generated with the blower 67b is heated with the heater 67h to generate hot wind, and this hot wind is supplied to the pressure chambers R63a and R63b of the partition member 63 in the case member 62 of the above-described heating unit 61 via an appropriate pipe member 67p. The hot wind then travels through the pressure chambers R63a and R63b and is blasted through the blast openings 63Na and 63Nb.

The blower 67b has an impeller 67i that rotates using a motor, for example, as a drive source, and an inverter (not shown) that adjusts the rotation speed (rpm) of the motor. Accordingly, it is possible to perform VVVF inverter control, thus making it possible to adjust the flow rate (m$^3$/min) to any value via a change in the rotation speed (rpm) of the impeller 67i.

Also, the heater is an electric heater that performs heating using electricity (kW) for example, and the temperature of the hot wind can be adjusted to any value by a change in the electricity input amount. Note that regarding the temperature of the hot wind, it is sufficient that the temperature at the positions of the blast openings 63Na and 63Nb is greater than or equal to a temperature that is 50° C. lower than the melting point of the thermoplastic resin fibers included in the non-woven fabric 3a, and also less than the melting point. Setting the temperature in this range makes it possible to reliably restore the bulk while also preventing melting of the thermoplastic resin fibers.

Note that the heater 67h may be built into the blower 67b as shown in FIG. 3A, or may be provided outside the blower 67b. In the case of providing the heater 67h on the outside, it is sufficient that heaters 67ha and 67hb are arranged adjacent to the case member 62 of the heating unit 61 as shown by virtual dashed double-dotted lines in FIG. 3A, and this configuration makes it possible to increase the response when adjusting the hot wind temperature. In this case, it is further preferable that the heaters 67ha and 67hb are provided one each for the blast openings 63Na and 63Nb. In other words, it is sufficient that the heater 67ha is provided in correspondence with the outgoing route blast opening 63Na, and the heater 67hb is separately provided in correspondence with the return route blast opening 63Nb. According to this configuration, it is possible to individually adjust the hot wind temperature for the blast openings 63Na and 63Nb, thus making it possible to perform bulk restoration processing with more precise condition settings.

Note that the heaters 67h, 67ha, and 67hb are not limited in any way to electric heaters, and any type of heater can be applied as long as it can heat a gas such as air that forms wind.

Also, although "wind" refers to a flow of air in this example, besides a flow of air, it broadly encompasses a flow of a gas such as nitrogen gas or an inert gas. In other words, nitrogen gas or the like may be blown out from the blast openings 63Na and 63Nb.

Adhesive application devices 81, 82

In the example in FIG. 2, two types of adhesive application devices 81 and 82 are provided to apply the hot-melt adhesive to the non-woven fabric 3a. Both the application devices 81 and 82 apply the adhesive to the non-woven fabric 3a at a position between a position on the downstream side of the heating unit 61 in the conveying direction and the position of the joining device 90.

The application devices 81 and 82 each have discharge portions 81a and 82a for discharging the adhesive, as well as a pump (not shown). The pumps pump the hot-melt adhesive to the discharge portions 81a and 82a in a fluid state, and thus the fluid adhesive is discharged from the discharge portions 81a and 82a.

Here, the one application device 81 of the two types is a contact application device, and the other application device 82 is a contactless application device. The contact application device 81 applies the adhesive with the discharge portion 81a in contact with or in the vicinity of the application target, whereas the contactless application device 82 applies the adhesive by dripping it from the discharge portion 82a that is sufficiently separated from the application target.

In the example in FIG. 2, firstly the contact application device 81 applies the adhesive to the non-woven fabric 3a, and thereafter the contactless application device 82 applies the adhesive at a downstream position.

The contact application device 81 applies the adhesive in a solid-coating application pattern in which the application target portions are the portions of the one surface of the non-woven fabric 3a that do not cover the absorbent bodies 4, 4 that is to say the portions of the one surface of the non-woven fabric 3a that are to be joined to the back sheet 5a. For this reason, the application device 81 has a nozzle shaped as a slit elongated in the CD direction as the discharge portion 81a, and thus whereas the adhesive is applied to the non-woven fabric 3a over approximately the entire length in the CD direction, the adhesive is discharged intermittently in the conveying direction such that the adhesive is selectively applied to only the aforementioned application target portions.

On the other hand, the contactless application device 82 applies the adhesive in a predetermined application pattern in which approximately the entirety of one surface of the non-woven fabric 3a is the application target portion. Here, this application pattern is a pattern in which multiple linear portions that are continuous in the conveying direction are lined up in the CD direction, and examples of the shapes of these linear portions include such as a straight line along the conveying direction, a spiral line along the conveying direction, and a wavy line along the conveying direction. In order to be able to perform application in this application pattern, the application device 82 has multiple approximately circular hole-shaped nozzles lined up in the CD direction as the discharge portion 82a, and the adhesive is applied to approximately the entirety of the one surface of the non-woven fabric 3a in this application pattern by continuously dripping the adhesive from each of the nozzles.

Note that as shown in FIG. 2, the contactless application device 82 is provided in the conveying route for the back sheet 5a as well. This application device 82 applies the adhesive over approximately the entirety of one surface of the back sheet 5a as well in the above-described application pattern, that is to say the pattern in which multiple linear portions that are continuous along the conveying direction are lined up in the CD direction.

Joining Device 90

As shown in FIG. 2, the joining device 90 has a pair of upper and lower rolls 90a and 90b that are driven to rotate about rotation shafts along the CD direction. The drive source of the pair of rolls 90a and 90b is a servo motor, for example. The pair of rolls 90a and 90b are rotated with the motor in directions opposite to each other with their outer circumferential surfaces opposing each other, and thus an object inserted between the pair of rolls 90a and 90b is clamped therebetween and carried out.

Meanwhile, the joining device 90 is arranged in an approximately straight line-shaped conveying route R4 along which the absorbent bodies 4 are conveyed. Specifically, as shown by the dashed double-dotted arrows in FIG. 2, the conveying route R4 for the absorbent bodies 4 passes through the position between the pair of rolls 90a and 90b in an approximately horizontal direction, and multiple absorbent bodies 4, 4 . . . are carried from the manufacturing apparatus for the absorbent body 4 along the conveying route R4 with a predetermined pitch P4. For this reason, rotation speed values V90a and V90b of the rolls 90a and 90b are subjected to coordination control so as to be approximately the same value as the conveying velocity value V4 of the absorbent body 4 in the conveying route R4.

As shown in FIG. 2, the bulk restoring device 20 is arranged directly above the conveying route R4 for the absorbent body 4, and therefore the non-woven fabric 3a whose bulk has been restored with the bulk restoring device 20 is fed to the joining device 90 from above the joining device 90. Specifically, the non-woven fabric 3a is wound around the upper roll 90a of the joining device 90 at a predetermined winding angle of 90° or the like and fed to a position between the pair of upper and lower rolls 90a and 90b in this manner.

Furthermore, due to the manner in which the non-woven fabric 3a is wound around and fed to the upper roll 90a, the back sheet 5a is wound around the lower roll 90b with a predetermined winding angle of 90° or the like and fed to a position between the pair of upper and lower rolls 90a and 90b in this manner.

The three materials 3a, 4, and 5a then together pass between the pair of upper and lower rolls 90a and 90b, and are clamped with the pair of rolls 90a and 90b as they pass through, and thus the three materials 3a, 4, and 5a are joined, and the continuous body 1a of pet sheets 1 is manufactured.

Here, as previously described, the non-woven fabric 3a is heated with the bulk restoring device 20. For this reason, the temperature at the point in time of being joined to both the non-woven fabric 3a and the back sheet 5a in the joining device 90 is higher than the temperature before being heated with the bulk restoring device 20. Accordingly, even in the state of being applied to the non-woven fabric 3a, the hot-melt adhesive has a low viscosity and is in a high fluidity state. Thus, the impregnation and permeation of the adhesive into the non-woven fabric 3a during joining proceeds smoothly, and the non-woven fabric 3a is joined to the absorbent body 4 and the back sheet 5a with high adhesion strength.

Note that the temperature of the non-woven fabric 3a at the time of this joining is preferably higher than 40° C., more preferably higher than 50° C., further preferably higher than 70° C., and even further preferably above the softening point. If such a temperature is reached, the impregnation and permeation of the adhesive into the non-woven fabric 3a during joining proceeds even more easily, and the non-woven fabric 3a is joined to the absorbent body 4 and the back sheet 5a with higher adhesion strength. It should be noted that the viscosity (viscosity (Pa·s)) of the hot-melt adhesive has a tendency to decrease rapidly at the softening point, and therefore achieving a temperature at or above the softening point is effective. The softening point can change according to the composition of the hot-melt adhesive, but broadly lies within the range of 80° C. to 120° C., and narrowly lies within the range of 80° C. to 100° C. Also, the range of the viscosity (Pa·s) of the hot-melt adhesive during joining is preferably, for example, 100 to 150000 (mPa·s), or more preferably 1000 to 10000 (mPa·s).

Note that aforementioned "temperature before the heating of the non-woven fabric 3a" refers to the temperature of the non-woven fabric 3a at a position just 5 meters to the upstream side of the case member 62 of the heating unit 61 in the conveying direction.

Incidentally, the arrival of the non-woven fabric 3a at the joining device 90 in a high temperature state in this way is mainly realized in this example with the bulk restoring device 20 being arranged directly above the conveying route R4 for the absorbent body 4. In other words, due to the bulk restoring device 20 being positioned directly above the conveying route R4 for the absorbent body 4, the bulk restoring device 20 is arranged in the vicinity of the joining device 90. For this reason, the bulk restoring device 20 and the joining device 90 can be connected with a relatively short conveying route length. Thus, the amount of temperature drop in the non-woven fabric 3a that has been heated with the bulk restoring device 20 is suppressed, and the non-woven fabric 3a can arrive at the position between the rolls 90a and 90b of the joining device 90 in a relatively high temperature state.

To give a more specific description of this, supposing that the bulk restoring device 20 is arranged at a position shifted laterally from the conveying route R4 for the absorbent body 4, that is to say shifted in the CD direction from the conveying route R4, the non-woven fabric 3a would need to be conveyed along the CD direction, and the conveying route length for reaching the joining device 90 would increase by a commensurate amount. Accordingly, there is a risk of the non-woven fabric 3*a* becoming excessively cooled before reaching the joining device 90, or the longer the conveying route length is, the greater the number of opportunities for being unintendedly cooled forcibly due to being subjected to cool air or the like in the conveying process.

However, in the case where the bulk restoring device 20 (the heating unit 61 in particular) is arranged directly above the conveying route R4 for the absorbent body 4 as described above, the conveying route length from after heating of the non-woven fabric 3*a* until arrival at the joining device 90 can be shortened, thus resulting in the ability to keep the temperature of the non-woven fabric 3*a* at a high temperature at the time of joining as described above.

It should be noted that in this example, the time required for the arrival of the non-woven fabric 3*a* at the joining device 90 after departing from the heating unit 61 of the bulk restoring device 20 is in the range of 0.2 seconds to 10 seconds. In the case where the required time falls within this range, as long as the non-woven fabric 3*a* is not forcibly cooled during conveying along the conveying route from the heating unit 61 to the joining device 90, the temperature of the non-woven fabric 3*a* at the time of arrival at the joining device 90 is reliably higher than the temperature of the non-woven fabric 3*a* before being heated with the bulk restoring device 20. In other words, as long as the non-woven fabric 3*a* is only cooled naturally during conveying along the conveying route, the temperature of the non-woven fabric 3*a* during joining can be kept at a higher temperature than before heating with no problem of any kind.

The above-described matter, however, does not in any way disallow the arrangement of the bulk restoring device 20 to the side of the conveying route R4 for the absorbent body 4. Specifically, even in the case where the device 20 is arranged to the side, as long as the temperature of the non-woven fabric 3*a* during joining with the joining device 90 can be kept at a high temperature as described above, the bulk restoring device 20 may be arranged at such a position to the side.

Also, although neither of the pair of upper and lower rolls 90*a* and 90*b* of the joining device 90 are heated with a heating device in the above example, they may be heated from the viewpoint of keeping the temperature of the non-woven fabric 3*a* at a high temperature during joining. For example, a configuration is possible in which at least the upper roll 90*a* of the pair of upper and lower rolls 90*a* and 90*b* of the joining device 90 is heated with an appropriate heating device or the like, thus keeping the temperature of the outer circumferential surface of upper roll 90*a* at or above the temperature that the non-woven fabric 3*a* was at the start of contact with the outer circumferential surface of the roll 90*a*, under the condition of not melting the non-woven fabric 3*a*. In this case, it is possible to suppress a decrease in the temperature of the non-woven fabric 3*a* that can occur while the non-woven fabric 3*a* moves over the 90° winding angle range on the upper roll 90*a*, and this also effectively contributes to achieving the high temperature state of the non-woven fabric 3*a* during joining. Note that an electric heater built into the upper roll 90*a* can be given as an example of the aforementioned heating device, and the same type of heating device may be provided for the lower roll 90*b*.

Also, the meaning of "directly above" in the above-described description "the bulk restoring device 20 (or the heating unit 61) is arranged directly above the conveying route R4 for the absorbent body 4" of course may be interpreted in a general sense, but in the case where a definition is presumed to be given, it would refer to an arrangement relationship in which in the case of being viewed in a plan view, that is to say in the case of being viewed from above, the bulk restoring device 20 (or the heating unit 61) appears to overlay the conveying route R4 for the absorbent body 4 from above, or more specifically, it would refer to an arrangement relationship in which at least a portion of the bulk restoring device 20 (or the heating unit 61) appears to overlay the movement locus R4 of the absorbent body 4.

Incidentally, in the example in FIG. 2, three pressing devices 95, 97, and 99 are separately provided at positions downstream of the joining device 90 in the conveying direction. The first pressing device 95 is a so-called light pressing device and very lightly presses approximately the entire surface of the continuous body 1*a* of pet sheets 1. Also, the second pressing device 97 is a so-called end pressing device and selectively presses portions of the continuous body 1*a* of pet sheets 1 where the absorbent body 4 does not exist, that is to say the portions between adjacent absorbent bodies 4, 4 in the conveying direction. The last third pressing device 99 is a so-called side edge pressing device that selectively presses portions of the continuous body 1*a* of pet sheets 1 where the absorbent body 4 does not exist, that is say the both end portions in the CD direction.

The inclusion of these three pressing devices 95, 97, and 99 makes it possible for the non-woven fabric 3*a*, the absorbent body 4, and the back sheet 5*a* to be joined with higher adhesion strength.

It should be noted that an apparatus having a pair of rolls 95*a* and 95*b* that rotate with smooth outer circumferential surfaces that oppose each other can be given as an example of the light pressing device 95. Also, the following apparatuses can be given as examples of the end pressing device 97 and the side edge pressing device 99. The end pressing device has a pair of rolls 97*a* and 97*b* that rotate with their outer circumferential surfaces opposing each other, and projection portions 97*ap*, 97*ap* that correspond to the portion between the absorbent bodies 4, 4 are provided on the outer circumferential surface of at least one roll 97*a* of the pair of the rolls 97*a* and 97*b*. Also, the side edge pressing device has a pair of rolls 99*a* and 99*b* that rotate with their outer circumferential surfaces opposing each other, a pair of ring-shaped projection portions 99*ap*, 99*ap* are respectively provided on the both end portions of the outer circumferential surface in the CD direction on at least the roll 99*a* of the pair of rolls 99*a* and 99*b*, and these projection portions 99*ap*, 99*ap* selectively press the portions of the continuous body 1*a* of pet sheets 1 where the absorbent body 4 does not exist, that is to say the both end portions in the CD direction. These pressing devices 95, 97, and 99 are not essential configurations, however, and can be omitted.

Other Embodiments

Although an embodiment of the present invention have been described above, the above embodiment is for facilitating understanding of the present invention and is not for interpreting the present invention in a limiting manner. Also, modifications and improvements that can be made without departing from the gist of the present invention, as well as equivalents thereof are, needless to say, encompassed within the present invention. For example, modifications such as the following are possible.

Although the non-woven fabric 3a for the top sheet 3a of the pet sheet 1 is given as an example of the processing target of the bulk restoring device 20 in the above-described embodiment, there is no limitation whatsoever to this. For example, the processing target may be a non-woven fabric for the top sheet of a sanitary napkin, or a non-woven fabric for the top sheet of a diaper. Also, the processing target of the bulk restoring device 20 is not limited in any way to being the non-woven fabric 3a for the top sheet 3a. In other words, a non-woven fabric for the material of another component required to have bulk may be processed with the bulk restoring device 20 of the present invention.

Although the absorbent body 4 and the back sheet 5a are given as examples of the "other member" to which the non-woven fabric 3a is joined in the above embodiment, there is no limitation whatsoever to this. For example, in the case of a sanitary napkin, a liquid-permeable second sheet is provided between the absorbent body 4 and the top sheet 3a that is the non-woven fabric 3a for the purpose of diffusion of a liquid, and therefore this second sheet may be joined to the non-woven fabric 3a as the "other member". Also, in the case of a disposable diaper, a barrier cuff sheet for forming a so-called barrier cuff is provided as the top sheet that is the non-woven fabric 3a, and therefore the barrier cuff sheet may be joined to the non-woven fabric 3a as the "other member".

The hot-melt adhesive is applied to the non-woven fabric 3a and the back sheet 5a, but not to the absorbent body 4 in the above embodiment, but there is no limitation whatsoever to this. For example, the hot-melt adhesive may be applied to the absorbent body 4 and the back sheet 5a, but not to the non-woven fabric 3a. Application to the non-woven fabric 3a, however, is preferable due to the impregnation and permeation of the adhesive into the non-woven fabric 3a progressing up to the time of arrival at the joining device 90.

In the case of application to the absorbent body 4, either the contact 81 or the contactless application device 82 described above can be used. It is preferable to use the contactless application device 82 in consideration of the fact that as the absorbent bodies 4 that are the application targets are conveyed by a belt conveyor CV with gaps therebetween in the conveying direction, it is possible for a level difference to arise between the portion of the belt conveyor CV that has the absorbent body 4 thereon and the portion that does not have the absorbent body 4 thereon.

Although the pair of upper and lower rolls 90a and 90b that rotate are given as an example of the joining device 90 in the above embodiment, there is no limitation whatsoever to this. Specifically, any device can be applied as long as it can stack the three members of the non-woven fabric 3a, the absorbent body 4, and the back sheet 5a in the thickness direction and press them in the thickness direction. For example, the joining device may be configured with an apparatus that has a pair of upper and lower endless belts that revolve with their outer circumferential surfaces opposing each other. In other words, the three members 3a, 4, and 5a may be joined by being inserted into and clamped between the revolving pair of upper and lower endless belts.

Although the non-woven fabric 3a is joined to both the absorbent body 4 and the back sheet 5a at the same time in the joining device 90 in the above embodiment, there is no limitation whatsoever to this. For example, the non-woven fabric 3a may be joined to only either one of the absorbent body 4 or the back sheet 5a. In other words, the timing of joining to the non-woven fabric 3a may be shifted ahead/behind between the absorbent body 4 and the back sheet 5a.

Although the non-woven fabric 3 having multiple straight line-shaped linear projection portions 3p, 3p . . . on one surface as shown in FIG. 1B is given as an example of the non-woven fabric 3 for the top sheet 3 in the above embodiment, there is no limitation whatsoever to this. For example, it may be a non-woven fabric in a normal mode, that is to say a non-woven fabric with approximately flat surfaces on both sides.

Although the heating unit 61 of the heating portion 60 heats the non-woven fabric 3a in both the outgoing route and the return route as shown in FIG. 2 in the above embodiment, there is no limitation whatsoever to this. For example, in the case where the bulk is sufficiently restored in only either one of the outgoing route or the return route, either one of the outgoing route blast opening 63Na or the return route blast opening 63Nb may be omitted. Conversely, in the case where bulk restoration is not sufficient with merely two paths, namely the outgoing route and the return route, multiple heating units 61 may be provided rather than merely the one heating unit 61, and the non-woven fabric 3a may be heated in three or more paths . Note that providing the blast openings 63Na and 63Nb in correspondence with the outgoing route and the return route is preferable due to shortening the dimension of the heating unit 61 in the lengthwise direction while also reliably ensuring a conveying route length for the non-woven fabric 3a that is needed for bulk restoration.

Although the heating unit 61 is configured in a system different from existing air-through systems as shown in FIGS. 3A and 3B in the above embodiment, there is no limitation whatsoever to this. Specifically, the heating unit may be configured in an existing air-through system. Note that a heating unit configured in an existing air-through system is as follows, for example. The heating unit has a hot wind blast opening provided so as to oppose one of the two surfaces of the non-woven fabric 3a conveyed along the conveying direction, and a hot wind suction opening provided so as to oppose the other one of the two surfaces. The blast opening and the suction opening both form a streamline in which hot wind blasted from the blast opening is suctioned with the suction opening, and thus the hot wind is passed through the non-woven fabric 3a in the thickness direction to heat the non-woven fabric 3a.

Note that a suction belt conveyor device, a suction drum device, and the like can be given as examples of the conveying mechanism that conveys the non-woven fabric 3a in the conveying direction. Specifically, the suction belt conveyor device conveys the non-woven fabric 3a in the state of being placed on the outer circumferential surface of an endless belt that is driven to revolve, and due to multiple suction holes being provided in the outer circumferential surface, the suction holes function as the above-described suction openings that suction the hot wind. Also, the suction drum device conveys the non-woven fabric 3a in the state of being wound around the outer circumferential surface of a rotating drum that is driven to rotate, and due to multiple suction holes being provided in the outer circumferential surface, the suction holes function as the above-described suction openings that suction the hot wind.

Figure 4:
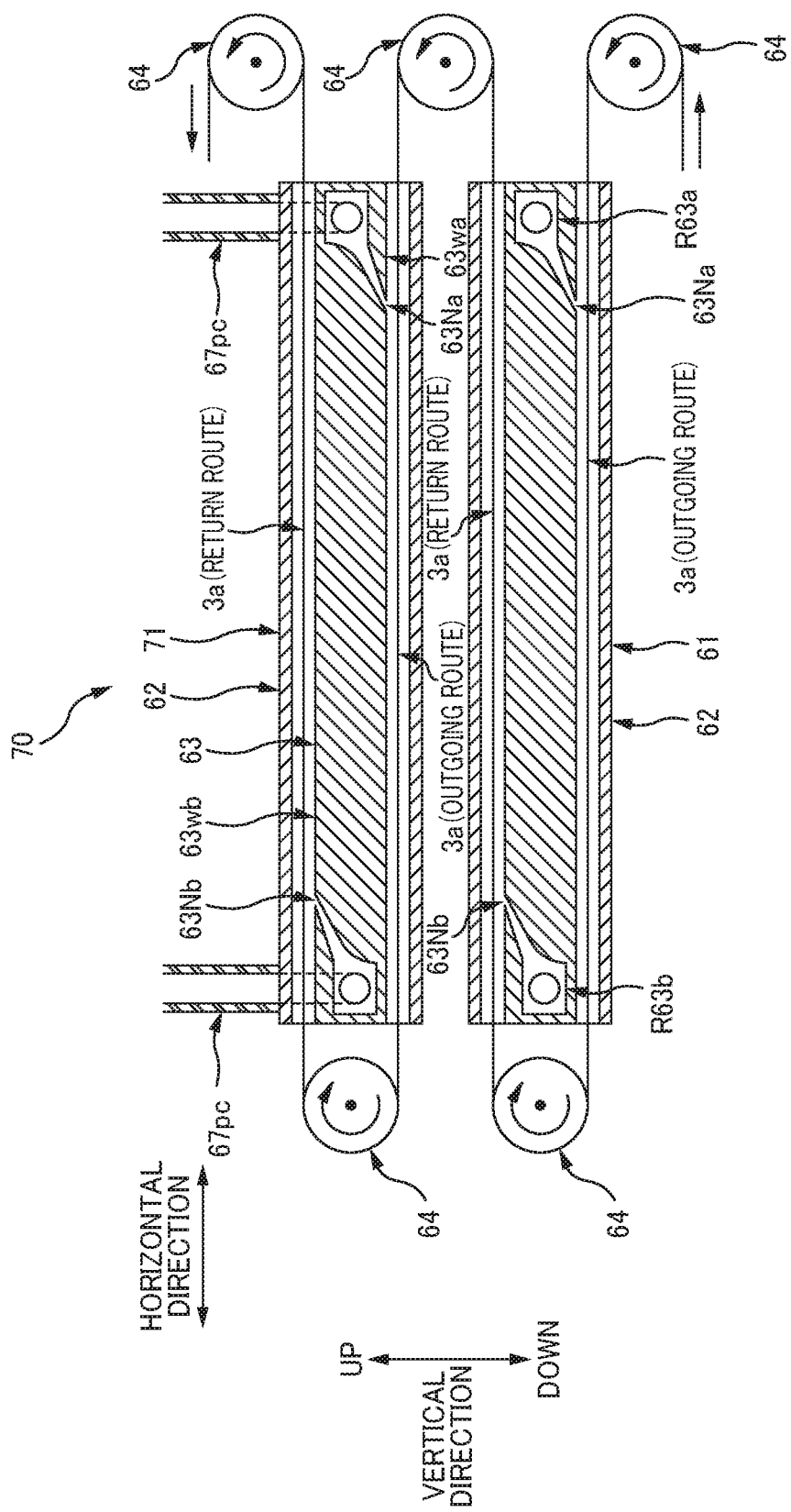
FIG. 4 is a schematic cross-sectional view of a cooling unit 71 added immediately downstream of a heating unit 61.
Figure 6A:
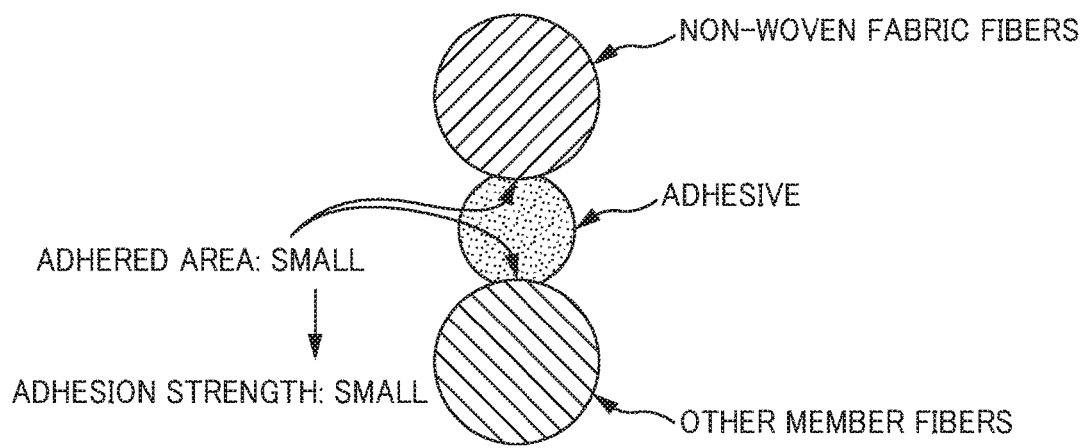
FIG. 6A is an illustrative cross-sectional diagram showing a state in which the area occupied by an adhesive is small on both the surface of fibers in a non-woven fabric and the surface of fibers in another member.
Figure 6B:
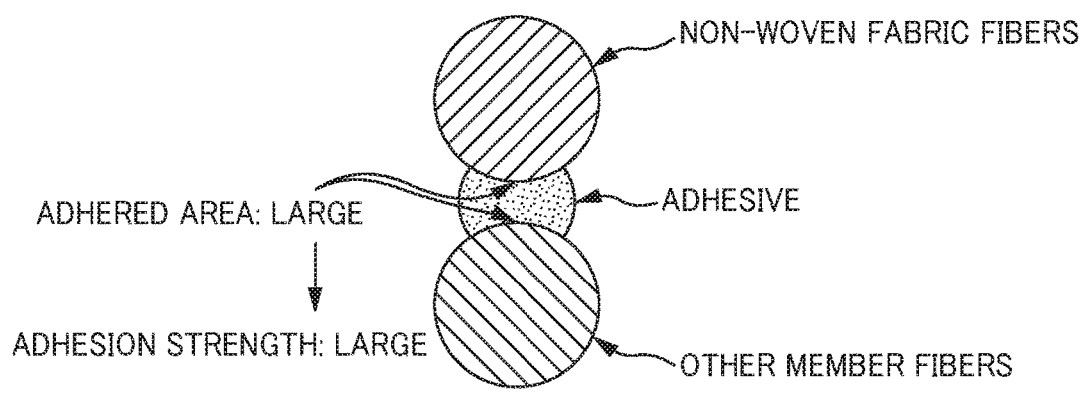
FIG. 6B is an illustrative cross-sectional diagram showing a state in which the area occupied with the adhesive is large on both the surface of fibers in the non-woven fabric and the surface of fibers in the other member.

Although the non-woven fabric 3a that has passed through the heating unit 61 of the heating portion 60 undergoes so-called natural cooling in the above embodiment, depending on the case, a cooling unit 70 (corresponding to a cooling device) that cools the non-woven fabric 3a at a position on the immediately downstream side of the heating unit 61 may be added as shown in FIG. 4.

Specifically, the cooling unit 70 is arranged at a position on the immediately downstream side of the heating unit 61, and has a cooling unit 71 that blows cooling wind onto the non-woven fabric 3*a* in order to cool it, and a wind supplying device (not shown) that supplies cooling wind to the cooling unit 71.

In the case where the non-woven fabric 3*a* is cooled with the cooling wind blasted from the cooling unit 71, it is possible to effectively suppress a phenomenon that can occur due to the temperature of the non-woven fabric 3*a* being high after being heated with the heating unit 61, that is to say a phenomenon in which the width-direction dimension varies due to softening of the non-woven fabric 3*a*.

Needless to say, however, the cooling unit 70 cools the non-woven fabric 3*a* with a higher temperature than the temperature before being heated with the heating unit 61 of the heating portion 60 as the lower limit value of the temperature of the non-woven fabric 3*a*. Accordingly, even in the case of being cooled with this cooling unit 71, the adhesive has a low viscosity and is kept in a high fluidity state at the time of joining of the non-woven fabric 3*a*, the absorbent body 4, and the back sheet 5*a*. As a result, during this joining, the impregnation and permeation of the adhesive into the non-woven fabric 3*a* proceeds smoothly, and it is possible to raise the adhesion strength between the non-woven fabric 3*a* and the absorbent body 4 and back sheet 5*a*.

A configuration similar to that of the previously-described heating unit 61 can be given as an example of the cooling unit 71. Specifically, the cooling unit 71 has a case member 62, a partition member 63, and guide rollers 64, 64, 64 similarly to the heating unit 61. However, wind with a temperature capable of cooling the non-woven fabric 3*a* is blasted from each of slit-shaped blast openings 63Na and 63Nb provided in both wall surfaces 63*wa* and 63*wb* of the partition member 63. In other words, for example, room-temperature wind or cool wind with a temperature lower than room temperature is supplied from the wind supplying device to the blast openings 63Na and 63Nb via an appropriate pipe member 67*pc*. For this reason, the wind supplying device has at least a blower, and preferably has a cooler that cools the wind generated with the blower. Note that the above-described wind can cool the non-woven fabric 3*a* in the case where its temperature is lower than the temperature of the non-woven fabric 3*a* immediately after exiting the case member 62 of the heating unit 61, and thus maybe higher than room temperature (20° C.±15° C.), such as being any value in the range of 5° C. to 50° C., for example, or may be set higher than this range depending on the case. According to the cooling unit 71 having this configuration, the cooling wind blasted from the blast openings 63Na and 63Nb flows over the surface of the non-woven fabric 3*a*, thus effectively preventing the non-woven fabric 3*a* from becoming compressed in the thickness direction. Thus, the loss of the restored bulk with the wind is effectively avoided.

Although the hot wind that has flowed through the outgoing route and return route spaces SP62*a* and SP62*b* is discharged as-is through the outlets 62*a*out and 62*b*out for the non-woven fabric 3*a* in the case member 62 in the above embodiment (FIG. 3A), from the viewpoint of energy reuse and from the viewpoint of mitigating adverse effects from the hot wind on other devices and other members in the vicinity, the hot wind that has flowed through the spaces SP62*a* and SP62*b* may be recovered and returned to the intake-side portion 67*bs* of the blower 67*b*. For example, as shown in the schematic cross-sectional view in FIG. 5, a configuration is possible in which openings 63*ha* and 63*hb* are provided in portions of the partition member 63 on the downstream side in the conveying direction, and pipe end opening portions on one side of recovery pipe members 69 are connected to the openings 63*ha* and 63*hb*, thus putting the spaces inside the pipe members 69 into communication with at least one of a downstream end portion SP62*ae* of the outgoing route space SP62*a* and a downstream end portion SP62*be* of the return route space SP62*b*, and putting the pipe end opening portions on the other side of the pipe members 69 into communication with the intake-side portion 67*bs* of the blower 67*b*.

In the case of the example in FIG. 5, there is a risk of foreign objects such as fiber scraps from the non-woven fabric 3*a* being sent through the recovery pipe members 69 to the heater 67*h* in the blower 67*b* and becoming fused thereto. For this reason, it is preferable that a mesh-like foreign object suction prevention filter member having a predetermined mesh, for example, is inserted between the recovery pipe members 69 and the intake-side portion 67*bs* of the blower 67*b*. Note that in the case of the example in FIG. 3A as well, there is a risk of foreign objects such as paper dust in the manufacturing line becoming mixed with the ambient air and suctioned through the intake-side portion 67*bs*, and thus it is preferable that the same type of filter member is provided in the intake-side portion 67*bs*.

In the above embodiment, as shown in FIG. 3A, the outgoing route blast opening 63Na is provided in the portion of the outgoing route wall surface 63*wa* on the upstream side in the outgoing route, and the return route blast opening 63Nb is provided in the portion of the return route wall surface 63*wb* on the upstream side in the return route, but there is no limitation whatsoever to this.

For example, a configuration is possible in which the outgoing route blast opening 63Na is provided in a portion of the outgoing route wall surface 63*wa* on the downstream side in the outgoing route (this corresponds to the "outlet-side portion of the case member"), and the return route blast opening 63Nb is provided in a portion of the return route wall surface 63*wb* on the downstream side in the return route (this corresponds to the "outlet-side portion of the case member"). Note that in this case, both of the outgoing route and return route blast openings 63Na and 63Nb are formed so as to blast hot wind toward the upstream side in the conveying direction with an acute angle of inclination relative to one of both the surfaces of the non-woven fabric 3*a*. Thus, the hot wind blasted from the outgoing route blast opening 63Na comes into contact with the surface of the non-woven fabric 3*a* with a velocity component in a direction toward the upstream side in the conveying direction, continues to flow upstream over the surface of the non-woven fabric 3*a*, and is ultimately discharged to the outside through the outgoing route inlet 62*a*in located most upstream in the outgoing route space SP62*a*. Also, the hot wind blasted from the return route blast opening 63Nb comes into contact with the surface of the non-woven fabric 3*a* with a velocity component in a direction toward the upstream side in the conveying direction, continues to flow to the upstream side over the surface of the non-woven fabric 3*a*, and is discharged to the outside through the return route inlet 62*b*in located the most upstream in the conveying direction in the return route space SP62*b*. The same applies to the above-described cooling unit 71 as well.

Although a solid member basically not having a space inside other than the pressure chambers R63*a* and R63*b* is used as the material for the partition member 63 in the above embodiment, there is no limitation whatsoever to this. For example, for the purpose of weight reduction or the like, a hollow member having a space inside may be used. One example that can be given for this hollow member is, for example, a combined member having a stainless steel flat plate member (not shown) that forms the outgoing route wall surface 63*wa* in FIG. 3A, a stainless steel flat plate member (not shown) that forms the return route wall surface 63*wb*, and a rectangular column member (not shown) that is inserted between these flat plate members and connects the flat plate members.

The invention claimed is:

1. A manufacturing method of manufacturing a sheet member of an absorbent article by joining a non-woven fabric to another member of the absorbent article, the manufacturing method comprising:
   restoring bulk of the non-woven fabric through heating the non-woven fabric by blowing hot wind onto the non-woven fabric while conveying the non-woven fabric along a conveying direction, the non-woven fabric being continuous in the conveying direction; and
   joining the non-woven fabric whose bulk has been restored with the hot wind to the other member using an adhesive, while the non-woven fabric being at a higher temperature than a temperature of the non-woven fabric before being heated with the hot wind,
   wherein
   the bulk of the non-woven fabric is restored by a bulk restoring device,
   the bulk restoring device has a case member provided with an inlet for the non-woven fabric and an outlet for the non-woven fabric,
   one of an inlet-side portion and an outlet-side portion of the case member has a blast opening and the other one of the inlet-side portion and the outlet-side portion has a discharge port, and
   said restoring includes
      blasting the hot wind from the blast opening into a space inside the case member toward the other one of the inlet-side portion and the outlet-side portion, and
      discharging, from the case member and through the discharge port, the hot wind that has flown, while being in contact with one surface of both surfaces of the non-woven fabric, through the space inside the case member.

2. The manufacturing method according to claim 1, further comprising
   cooling, by a cooling device of the bulk restoring device, the non-woven fabric that has been heated with the hot wind, before the non-woven fabric is joined to the other member,
   wherein the cooling device cools the non-woven fabric at a cooling temperature higher than the temperature of the non-woven fabric before the non-woven fabric is heated, the cooling temperature being a lower limit temperature of the non-woven fabric.

3. The manufacturing method according to claim 2, wherein
   the cooling device has a further case member provided with an inlet for the non-woven fabric and an outlet for the non-woven fabric,
   in the cooling device, one of an inlet-side portion and an outlet-side portion of the further case member has a blast opening, and the other one of the inlet-side portion and the outlet-side portion of the further case member has a discharge port,
   the cooling, by the cooling device, includes
      blasting cooling wind from the blast opening of the further case member into a space inside the further case member toward the other one of the inlet-side portion and the outlet-side portion of the further case member, and
      discharging, from the further case member and through the discharge port of the further case member, the cooling wind that has flown, while being in contact with one surface of both surfaces of the non-woven fabric, through the space inside the further case member.

4. The manufacturing method according to claim 1, wherein
   the adhesive is a thermoplastic adhesive, and
   the adhesive is applied to at least the non-woven fabric.

5. The manufacturing method according to claim 1, wherein
   said blasting the hot wind onto the non-woven fabric includes blowing, by a heating unit of the bulk restoring device, the hot wind onto the non-woven fabric,
   wherein
   the heating unit is arranged directly above a conveying route along which the other member is conveyed, and
   the non-woven fabric that has been heated with the heating unit merges into the conveying route for the other member in a joining device.

6. The manufacturing method according to claim 5, wherein
   the conveying route for the non-woven fabric under the heating unit is oriented along a horizontal direction.

7. The manufacturing method according to claim 5, wherein
   the joining device has a pair of rolls that rotate with outer circumferential surfaces of the rolls opposing each other, and
   when the non-woven fabric and the other member are passed between the pair of rolls in a state laid on each other, the non-woven fabric and the other member are joined with the adhesive due to being clamped with the pair of rolls.

8. The manufacturing method according to claim 1, further comprising:
   applying, by an adhesive application device, the adhesive to at least one of the other member and the non-woven fabric whose bulk has been restored with the bulk restoring device.

9. The manufacturing method according to claim 8, wherein
   the adhesive application device applies the adhesive to the non-woven fabric in a position on a downstream side of the bulk restoring device in the conveying direction.

10. The manufacturing method according to claim 1, wherein, in said blasting, the blast opening blasts the hot wind into the space inside the case member toward the other one of the inlet-side portion and the outlet-side portion at an acute angle of inclination relative to the one surface of the non-woven fabric.

* * * * *